(12) United States Patent  (10) Patent No.: US 7,897,400 B2
Timmins et al.  (45) Date of Patent: Mar. 1, 2011

(54) **NON-INVASIVE RAPID DIAGNOSTIC TEST FOR *M. TUBERCULOSIS* INFECTION**

(75) Inventors: Graham Timmins, Albuquerque, NM (US); Vojo P. Deretic, Placitas, NM (US)

(73) Assignee: STC.UNM, Albuquerque, NM (US)

( * ) Notice: Subject to any disclaimer, the term of this patent is extended or adjusted under 35 U.S.C. 154(b) by 493 days.

(21) Appl. No.: 11/955,773

(22) Filed: Dec. 13, 2007

(65) Prior Publication Data

US 2009/0191639 A1    Jul. 30, 2009

Related U.S. Application Data

(60) Provisional application No. 60/925,297, filed on Apr. 19, 2007, provisional application No. 60/874,872, filed on Dec. 13, 2006.

(51) Int. Cl.
  *G01N 33/00* (2006.01)
  *A61K 31/44* (2006.01)
(52) U.S. Cl. ............. 436/63; 514/354; 514/277; 514/183
(58) Field of Classification Search ................... 436/63; 514/354, 183, 277
  See application file for complete search history.

(56) References Cited

U.S. PATENT DOCUMENTS

| | | | |
|---|---|---|---|
| 5,851,763 | A | 12/1998 | Heym et al. |
| 7,717,857 | B2 | 5/2010 | Timmins |
| 2003/0232020 | A1 | 12/2003 | York et al. |
| 2004/0224918 | A1 | 11/2004 | Yatvin et al. |
| 2004/0259806 | A1 | 12/2004 | Kolobov et al. |

OTHER PUBLICATIONS

Allen, T.H. et al., Colorimetric Determination of Carbon Monoxide in Air by an Improved Palladium Chloride Method, The Journal of Biological Chemistry 216:309-317 (1955).
Carterson, A.J. et al., The Transcriptional Regulator AlgR Controls Cyanide Production in *Pseudomonas aeruginosa*, Journal of Bacteriology 186:6837-6844 (2004).
Castric, P.A., Glycine Metabolism by *Pseudomonas aeruginosa*: Hydrogen Cyanide Biosynthesis, Journal of Bacteriology 130:826-831 (1977).

(Continued)

*Primary Examiner* — Walter D Griffin
*Assistant Examiner* — Christine T Mui
(74) *Attorney, Agent, or Firm* — Henry D. Coleman; R. Neil Sudol; William J. Sapone

(57) ABSTRACT

This invention relates to a test for detecting a *Mycobacterium tuberculosis* (tuberculosis or TB) infection in a patient or subject, specifically a diagnostic test, including a breath test, whereby patients are provided a small dose of an isotopically labeled TB drug, Isoniazid (INH) orally or directly to the lungs of the patient or subject. If TB is present, a TB enzyme mycobacterial peroxidase KatG oxidizes the INH; and KatG specific metabolites, in particular, isotopically labeled nitric oxide (NO), nitrites, nitrates, carbon monoxide (CO) or carbon dioxide converted from carbon monoxide of INH cleavage are measured. Other embodiments relate to a diagnostic breath test for detecting TB utilizing isotopically labeled urea (preferably, carbon-13 labeled urea), alone or in combination with isotopically labeled isoniazid (preferably, nitrogen-15 labeled isoniazid), wherein *M. tuberculosis* organism, if present in the patient or subject's lungs (or other tissues), will metabolize the isotopically labeled urea to isotopically labeled carbon dioxide ($CO_2$) such that a determination of the residence of *M. tuberculosis*, including residence of an isoniazid resistant strain of *M. tuberculosis*, may be made.

29 Claims, 3 Drawing Sheets

OTHER PUBLICATIONS

Cobb, L.M., et al., *Pseudomonas aeruginosa* Flagellin and Alginate Elicit Very Distinct Gene Expression Patterns in Airway Epithelial Cells: Implications for Cystic Fibrosis Disease, The Journal of Immunology 173:5659-5670 (2004). Firoved, A. M. et al., Microarray Analysis Reveals Induction of Lipoprotein Genes in Mucoid *Pseudomonas aeruginosa*: Implications for Inflammation in Cysitc Fibrosis, Infection and Immunity 72:5012-5018 (2004).

Firoved, A.M. et al., Microarray Analysis of Global Gene Expression in Mucoid *Pseudomonas aeruginosa*, Journal of Bacteriology 185:1071-1081 (2003).

Gallagher, L.A. et al., *Pseudomonas aeruginosa* PAO1 Kills *Caenorhabditis elegans* by Cyanide Poisoning, Journal of Bacteriology 183:6207-6214 (2001).

Goldberg, J.B. et al., The role of the CFTR in susceptibility to *Pseudomonas aeruginosa* infections in cystic fibrosis, Trends in Microbiology 8:514-520 (2000).

Govan, J.R.W. et al., Microbial Pathogenesis in Cystic Fibrosis: Mucoid *Pseudomonas aeruginosa* and *Burkholderia cepacia*, Microbiological Reviews 60:539-574 (1996).

Karmali, K. et al., The use of Fourier transform infrared spectroscopy to assay for urease from *Pseudomonas aeruginosa* and *Canavalia ensiformis*, Analytical Biochemistry 331:115-121 (2004).

Martin, D.W. et al., Mechanism of conversion to mucoidy in *Pseudomonas aeruginosa* infecting cystic fibrosis patients, Proc. Natl. Acad. Sci. USA 90:8377-8381 (1993).

Ramsey, D. M. et al., Understanding the control of *Pseudomonas aeruginosa* alginate synthesis and the prospects for management of chronic infections in cystic fibrosis, Molecular Microbiology 56:308-322 (2005).

Timmins, G.S., S. Master, F. Rusnak, and V. Deretic, (2004) Requirements for nitric oxide generation from isoniazid activation in vitro and inhibition of mycobacterial respiration in vivo, J Bacteriol. 186: 5427-5431.

Timmins, G.S., S. Master, F. Rusnak, and V. Deretic (2004) Nitric oxide generated from isoniazid activation by KatG: source of nitric oxide and activity against *Mycobacterium tuberculosis*, Antimicrob Agents Chemother. 48: 3006-3009.

Timmins, G.S. and V. Deretic, (2006) Mechanisms of action of isoniazid, Mol Microbiol. 62: 1220-1227.

Wayne, L.G., (1974) Simple pyrazinamidase and unease tests for routine identification of mycobacteria, Am Rev Respir Dis. 109: 147-151.

1. Labeled urea to lung

2. Urease positive TB in lung converts *Urea to *$CO_2$. Detection of *$CO_2$ diagnoses TB infection

NON-INVASIVE RAPID DIAGNOSTIC TEST FOR *M. TUBERCULOSIS* INFECTION

RELATED APPLICATIONS

This application claims the benefit of provisional application Ser. No. US60/874,872, filed Dec. 13, 2006, and provisional application Ser. No. US60/925,297, filed Apr. 19, 2007, the entire contents of both applications being incorporated by reference in their entirety herein.

FIELD OF THE INVENTION

This invention relates to a test for detecting a *Mycobacterium tuberculosis* (tuberculosis or TB) infection in a patient or subject in the lungs or systemically, specifically a diagnostic test, including a breath test, whereby patients are provided a small dose of an isotopically labeled TB drug, Isoniazid (INH) orally or directly to the lungs (or other tissue) of the patient or subject. If TB is present, a TB enzyme mycobacterial peroxidase KatG oxidizes the INH; and KatG specific metabolites, in particular, isotopically labeled nitric oxide (NO), nitrites, nitrates, carbon monoxide (CO) or carbon dioxide converted from carbon monoxide of INH cleavage are measured. Other embodiments relate to a diagnostic breath test for detecting TB utilizing isotopically labeled urea (preferably, carbon-13 labeled urea), alone or in combination with isotopically labeled isoniazid (preferably, nitrogen-15 labeled isoniazid), wherein *M. tuberculosis* organism, if present in the patient or subject's lungs (or other tissues), will metabolize the isotopically labeled urea to isotopically labeled carbon dioxide ($CO_2$) such that a determination of the residence of *M. tuberculosis*, including residence of an isoniazid resistant strain of *M. tuberculosis*, may be made.

BACKGROUND OF THE INVENTION

There is no currently available method to unambiguously and rapidly determine whether a person is actively infected with *Mycobacterium tuberculosis* or isoniazid resistant *Mycobacterium tuberculosis*. Skin tuberculin testing with purified protein derivative (PPD), is a useful first screen for potential exposure to mycobacteria but does not differentiate between prior exposure or currently active infection; chest X-rays only identify advanced lung lesions; a smear test is highly reliable but of low sensitivity since many TB patients do not present as smear positive; sputum culture of slow-growing TB bacteria is a definitive test but takes a long time and only detects active disease. This lack of an optimal test is a long-felt need with important implications. One of the most important aspects is that an improved test which will allow vaccination against TB using the BCG vaccine without impairing the ability of the diagnostic test to reliably predict the existence of TB infection despite vaccination, would make vaccination with BCG a viable choice for healthcare consumers who wish to make informed healthcare decisions. Moreover, by no longer relying upon current tuberculin testing, the benefits of BCG vaccination could be used in certain populations (e.g. troops and related personnel at risk of TB infection in areas with high incidence of TB). But since TB may become more widespread, and has potential for bioterror use, general use for the US population might also be an option. Another important aspect is that diagnosis of active TB can be made rapidly at a point of care, so that treatment can begin immediately, and so can help prevent further spread of the disease compared to diagnostic modalities that require long waiting periods between sampling and diagnosis.

BRIEF DESCRIPTION OF THE INVENTION

Figure 1:
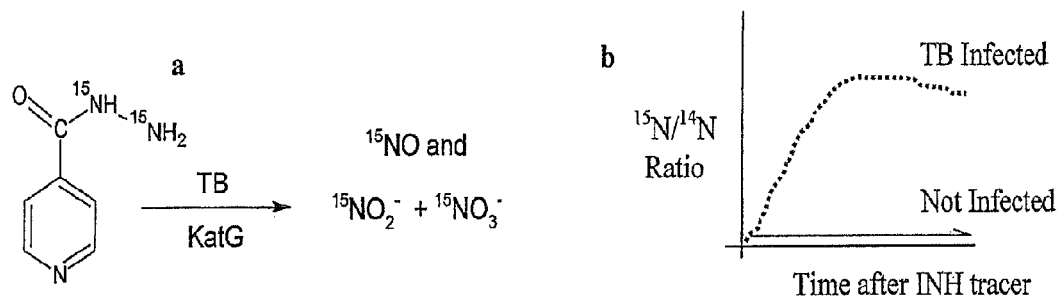
FIG. 1 shows a) TB specific metabolism of $^{15}N$—INH to products (nitric oxide, nitrite and nitrate) and b) a preferred approach for readout of infection using a ratio of isotopically labeled nitrogen to non-isotopically labeled nitrogen which is found in nitric oxide exhaled from a subject having been administered isotopically (Nitrogen-15) labeled isoniazid. Note that as the graph of the ratio of nitrogen-15/nitrogen-14 versus time becomes steeper, or as the plateau value becomes higher, that is evidence of a more severe *M. tuberculosis* infection.

The present invention relates to a method for identifying the existence of a *Mycobacterium tuberculosis* (tuberculosis) infection in the lungs (or other tissues in the case of systemic tuberculosis infection) of subject to be diagnosed, and optionally, whether or not the strain of *M. tuberculosis* residing in the subject's lungs (or other tissues) is susceptible or resistant to isoniazid, an agent typically used to treat *M. tuberculosis* infections.

According to the present invention there is provided a method for the diagnosis of *Mycobacterium tuberculosis* in the lungs (or other tissues) of a patient or subject, including the steps of:

(a) administering isotopically labeled isoniazid and/or urea to the subject, said isoniazid being cleavable by mycobacterial peroxidase KatG and said urea being cleavable by urease to form a cleavage product; and (b) analyzing a plurality of exhaled breaths of the subject for a concentration of said cleavage product(s), said concentration indicating the presence or absence of *M. tuberculosis* including optionally, the presence of isoniazid resistant *M. tuberculosis* in the lungs (or other tissues) of the subject (by virtue of INH-resistant TB not cleaving INH). Optional steps include fitting the concentrations to a curve; and analyzing the curve or plateau to determine the extent of infection.

Preferably, the step of analyzing the exhaled breath of the subject is repeated substantially at a particular time or times until a predetermined time period (which can range from as little as several breaths in a short period to a number of breaths in several minutes or more) has elapsed. This can be done by collecting breaths from a subject over a predetermined period of time or times. The predetermined period of time may be determined by analyzing the activity of control subjects with

*M. tuberculosis* infections to cleave isotopically labeled isoniazid and/or urea and measuring the concentration of isotopically labeled nitrogen, carbon and/or oxygen which is found in the exhaled breath of the control subjects as a function of time after administration of isoniazid and/or urea.

The exhaled breath of the subject is analyzed for content of the isotopically labeled element which evidences the residence of *M. tuberculosis*. In certain embodiments, the step of analyzing the exhaled breath of the subject is repeated substantially until a particular accuracy for analyzing the data is reached. In certain preferred aspects of the invention, a ratio of the concentration of an isotopically labeled element to a non-isotopically labeled element measured for a sample taken at one or more predetermined times and for one or more predetermined periods is calculated and a graph of the ratio (y-axis) as a function of time (x-axis) is provided. Exemplary graphs appear in FIGS. 1*b* and 2*b*. Preferably, the breath of the subject is analyzed by an infrared laser spectrometer or a mass spectrometer to determine concentrations of isotopically labeled elements and non-isotopically labeled elements. In a particularly preferred clinical diagnostic embodiment, a breath test according to the present invention will be designed to determine the existence of active *M. tuberculosis*, including an active isoniazid resistant strain of *M. tuberculosis.*

According to further preferred embodiments of the present invention, the isoniazid and/or urea is isotopically-labelled. In the case of isotopically labeled isoniazid, the cleavage product is preferably nitric oxide and/or carbon monoxide (which can be readily converted to carbon dioxide), and the nitric oxide is nitrogen-15 and/or oxygen-17 and/or oxygen-18 labeled, whereas the carbon monoxide/carbon dioxide is C-13 labeled and/or oxygen-17 and/or oxygen-18 labeled. Preferably, the isoniazid is labeled with nitrogen-15, carbon-13, oxygen-17, oxygen-18 or mixtures thereof. In isotopically labeled isoniazid, the carbon monoxide/carbon dioxide cleavage product is preferably carbon-13 isotopically-labelled. Alternatively and preferably, the cleavage product is nitric oxide and the nitric oxide is N-15 labeled ammonia. It is noted that although it is preferable to analyze for isotopically labeled nitric oxide and/or carbon monoxide/carbon dioxide in the breath of a subject, it is also possible to analyze for isotopically labeled nitrites and nitrates, or dissolved $CO_2$/bicarbonate in the blood (plasma, serum) or urine of a subject as alternative cleavage products of isoniazid.

In the case of the use of isotopically labeled urea, urea may be labeled with isotopically labeled carbon-13, nitrogen-15, oxygen-17 and/or oxygen 18, wherein the cleavage products to be analyzed from urea being acted upon by *M. tuberculosis* urease are isotopically labeled carbon dioxide and/or ammonia.

The present invention also relates to pharmaceutical compositions comprising effective amounts of isoniazid and urea in pulmonary dosage form. This composition comprises isoniazid and urea in effective amounts, in combination with a pharmaceutically acceptable carrier, additive or excipient, as well as a propellant and optionally, a solvent and/or a dispersant.

The present invention also relates to an oral dosage form comprising effective amounts of isoniazid and urea, optionally in combination with a pharmaceutically acceptable carrier, additive or excipient and further optionally in combination with an effective amount of a urease inhibitor.

In another aspect of the invention, a kit for diagnosing TB in a subject or patient comprises a composition comprising at least one compound selected from the group consisting of isotopically labeled isoniazid, preferably nitrogen-15 labeled isoniazid, isotopically labeled urea, preferably carbon-13 isotopically labeled urea and mixtures thereof in oral or pulmonary dosage form, a collection bag or vial to collect exhaled breaths from said subject or patient; and an optional instruction manual. In preferred aspects, the composition will comprise a combination of nitrogen-15 isotopically labeled isoniazid and carbon-13 isotopically labeled urea in pulmonary dosage form. In oral dosage form, a combination of nitrogen-15 isotopically labeled isoniazid and carbon-13 isotopically labeled urea are combined with an optional effective amount of a urease inhibitor as otherwise disclosed herein.

DETAILED DESCRIPTION OF INVENTION

The following terms are used to describe the present invention. In the event that a term is not specifically defined herein, that term is accorded its commonly understood meaning within the context of its use by those of ordinary skill in the art. It is understood that the definitions of the terms which are used to describe the present invention are interpreted in a manner consistent with the present invention and within the context of a particular term's use in describing the present invention.

As used herein and in the appended claims, the singular forms "a," "an," and "the" include plural reference unless the context clearly dictates otherwise. Thus, for example, a reference to "an isotopically labeled element" includes a plurality (for example, two or more elements) of such elements, and so forth. Under no circumstances is the patent be interpreted to be limited to the specific examples or embodiments or methods specifically disclosed herein.

The term "patient" or "subject" is used to describe an individual subject or patient, a mammal, generally a human, who has been exposed to tuberculosis, is suspected of having been exposed to tuberculosis or is to be diagnosed for possible exposure to tuberculosis using one or more methods according to the present invention.

The term "effective" refers to an amount of a substrate (i.e., isotopically labeled isoniazid, isotopically labeled urea or mixtures of these two) which is sufficient to produce a detectable level of a cleavage product or products, without an untoward level of adverse side effects, such as toxicity, irritation, allergy or hypersensitivity responses. The level of any such side effects should be commensurate with acceptable risk/benefit ratios. In the present invention, the term effective is used to describe an amount of a substrate or other substance which is used to effect an intended result within the context of its use.

The term "coadministration" is used to describe the administration of two active compounds, in this case isoniazid and urea, in effective amounts. Although the term coadministration preferably includes the administration of two active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

The term "cleaves" or "cleavage product" is used with reference to the fact that an enzyme of *M. tuberculosis* can break or metabolize at least one chemical bond of isoniazid or urea, forming "cleavage products" (nitric oxide, nitrite, nitrates, carbon monoxide/carbon dioxide, ammonia, etc), by chemical processes including, but not limited to, hydrolysis or oxidation/reduction. In the present invention, the concentration of the cleavage product or products (in the breath, serum, plasma or urine of a subject or patient) indicates the level of activity of *M. tuberculosis* species in the lungs (or other tissues) of the subject, which can be used to determine a diagnosis of infection by *M. tuberculosis*, and the intensity of the infection. A positive diagnosis indicates that *M. tuberculosis* is present in the lungs (or other tissues) of the subject. In preferred aspects of the invention, the method for diagnosis is preferably a "breath test", due to its ease of use by analyzing the breath of the subject for evidence of cleavage product.

Examples of appropriate labels for the substrate, and hence for the cleavage product or products, are those which can be detected by an appropriate measuring instrument, but which are substantially not harmful or toxic to the subject including, but not limited to, carbon-13 or carbon-14, oxygen-18 or nitrogen-15, isotope-labelling. An isotope is a form of an element, such as carbon, with a specific mass. For example, carbon-12 has a mass of 12 atomic mass units. The term "isotope-labeling" means that the naturally more abundant isotope of each of these elements is at least partially replaced by a less abundant isotope. For example, the naturally more abundant carbon-12 atoms could be at least partially replaced by the less abundant carbon-13 atoms, permitting the cleavage product or products which carry the label to be more easily detected, since the less abundant isotope can be distinguished from the naturally more abundant isotope. Furthermore, the advantage of certain isotopes such as carbon-13 is that they are stable, so that they are not radioactive, unlike isotopes such as carbon-14. Note that carbon 14 may be used in rare instances in an animal experimentation setting, but is inappropriate for use in a therapeutic setting. Therefore, preferably stable, non-radioactive isotopes such as carbon-13 are used as labels.

The term "isotopically labeled" shall mean isotopically labeled with carbon-13, nitrogen-15, oxygen-17 or oxygen-18 at positions on the isoniazid molecule or urea which give rise to isotopically labeled cleavage products as otherwise disclosed herein after exposure to *M. tuberculosis* enzymes mycobacterial peroxidase KatG and urease, respectively.

The term "Tuberculosis" or "TB" is used to describe the infection caused by the infective agent "*Mycobacterium tuberculosis*" or "*M. tuberculosis*", a tubercle *bacillus* bacteria. Tuberculosis is a potentially fatal contagious disease that can affect almost any part of the body but is most frequently an infection of the lungs. It is caused by a bacterial microorganism, the tubercle *bacillus* or *Mycobacterium tuberculosis*.

Tuberculosis is primarily an infection of the lungs, but any organ system is susceptible, so its manifestations may be varied. Effective therapy and methods of control and prevention of tuberculosis have been developed, but the disease remains a major cause of mortality and morbidity throughout the world. The treatment of tuberculosis has been complicated by the emergence of drug-resistant organisms, including multiple-drug-resistant tuberculosis, especially in those with HIV infection.

*Mycobacterium tuberculosis*, the causative agent of tuberculosis, is transmitted by airborne droplet nuclei produced when an individual with active disease coughs, speaks, or sneezes. When inhaled, the droplet nuclei reach the alveoli of the lung. In susceptible individuals the organisms may then multiply and spread through lymphatics to the lymph nodes, and through the bloodstream to other sites such as the lung apices, bone marrow, kidneys, and meninges.

The development of acquired immunity in 2 to 10 weeks results in a halt to bacterial multiplication. Lesions heal and the individual remains asymptomatic. Such an individual is said to have tuberculous infection without disease, and will show a positive tuberculin test. The risk of developing active disease with clinical symptoms and positive cultures for the tubercle *bacillus* diminishes with time and may never occur, but is a lifelong risk. Approximately 5% of individuals with tuberculous infection progress to active disease. Progression occurs mainly in the first 2 years after infection; household contacts and the newly infected are thus at risk.

Many of the symptoms of tuberculosis, whether pulmonary disease or extrapulmonary disease, are nonspecific. Fatigue or tiredness, weight loss, fever, and loss of appetite may be present for months. A fever of unknown origin may be the sole indication of tuberculosis, or an individual may have an acute influenzalike illness. Erythema nodosum, a skin lesion, is occasionally associated with the disease.

The lung is the most common location for a focus of infection to flare into active disease with the acceleration of the growth of organisms. Infections in the lung are the primary focus of the present invention. There may be complaints of cough, which can produce sputum containing mucus, pus-and, rarely, blood. Listening to the lungs may disclose rales or crackles and signs of pleural effusion (the escape of fluid into the lungs) or consolidation if present. In many, especially those with small infiltration, the physical examination of the chest reveals no abnormalities.

Miliary tuberculosis is a variant that results from the blood-borne dissemination of a great number of organisms resulting in the simultaneous seeding of many organ systems. The meninges, liver, bone marrow, spleen, and genitourinary system are usually involved. The term miliary refers to the lung lesions being the size of millet seeds (about 0.08 in. or 2 mm). These lung lesions are present bilaterally. Symptoms are variable.

Extrapulmonary tuberculosis is much less common than pulmonary disease. However, in individuals with AIDS, extrapulmonary tuberculosis predominates, particularly with lymph node involvement, with some pulmonary impact. For example, fluid in the lungs and lung lesions are other common manifestations of tuberculosis in AIDS. The lung is the portal of entry, and an extrapulmonary focus, seeded at the time of infection, breaks down with disease occurring.

Development of renal tuberculosis can result in symptoms of burning on urination, and blood and white cells in the urine; or the individual may be asymptomatic. The symptoms of tuberculous meningitis are nonspecific, with acute or chronic fever, headache, irritability, and malaise.

A tuberculous pleural effusion can occur without obvious lung involvement. Fever and chest pain upon breathing are common symptoms. Bone and joint involvement results in pain and fever at the joint site. The most common complaint is a chronic arthritis usually localized to one joint. Osteomyelitis is also usually present. Pericardial inflammation with fluid accumulation or constriction of the heart chambers secondary to pericardial scarring are two other forms of extrapulmonary disease.

At present, the principal methods of diagnosis for pulmonary tuberculosis are the tuberculin skin test (an intracutaneous injection of purified protein derivative tuberculin is performed, and the injection site examined for reactivity), sputum smear and culture, and the chest x-ray. Culture and biopsy are important in making the diagnosis in extrapulmonary disease.

A combination of two or more drugs is often used in the initial therapy of tuberculous disease. Drug combinations are used to lessen the chance of drug-resistant organisms surviving. The preferred treatment regimen for both pulmonary and extrapulmonary tuberculosis is a 6-month regimen of the antibiotics isoniazid, rifampin, and pyrazinamide given for 2 months, followed by isoniazid and rifampin for 4 months. Because of the problem of drug-resistant cases, ethambutol can be included in the initial regimen until the results of drug susceptibility studies are known. Once treatment is started, improvement occurs in almost all individuals. Any treatment failure or individual relapse is usually due to drug-resistant organisms.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

DESCRIPTION OF PREFERRED EMBODIMENTS

The present invention is a diagnostic test, preferably a breath test, which can be used to rapidly and accurately detect the presence of *M. tuberculosis*, and in certain preferred aspects, isoniazid resistant *M. tuberculosis* in the lungs (or other tissues) of a patient or subject. Specifically, the present invention can be used to diagnose the presence of *M. tuberculosis* by the administration (preferably pulmonary/intratracheal administration) of a safe and effective amount of isotopically labeled isoniazid and/or urea to a subject and then detecting the concentration of at least one of the cleavage products of isoniazid and/or urea in breath exhaled by the subject. In preferred aspects of the invention, several breaths taken at a predetermined time after administration of isoniazid and/or urea is sufficient for providing a measure of isotopically labeled nitrogen, carbon or oxygen. If the ratio of measured isotopically labeled element to non-isotopically labeled element is greater than a predetermined value, both the existence, the sensitivity to isoniazid and in many cases the severity of the *M. tuberculosis* infection may be readily determined.

Thus, in the case of isoniazid, detection of isotopically labeled nitrogen-15, carbon-13 or oxygen-17/18 in nitric oxide and/or carbon monoxide/carbon dioxide in the exhaled breath of the subject after a suitable period of time after administration (depending upon the route of administration) can provide diagnostic information about the existence of *M. tuberculosis* in the subject's lungs (or other tissues). In the case of urea, isotopically labeled carbon-13, nitrogen 15 or oxygen 17/18 in carbon dioxide or ammonia, or both cleavage products, measured in the exhaled breath of the patient or subject, after a suitable time period has elapsed, can also provide diagnostic information about the existence of *M. tuberculosis* infection in the subject's lungs (or other tissues).

In a preferred embodiment, isotopically labeled isoniazid and urea are administered to the subject to be tested for *M. tuberculosis* infection and, depending on the existence of cleavage products (or their absence) measured in the exhaled breath of the subject to be tested, diagnostic information may be used to determine whether or not there is a *M. tuberculosis* infection in the lungs (or other tissues) of the subject tested and whether, if there such an infection, whether that infection is isoniazid sensitive or is isoniazid resistant. In preferred aspects of the invention, a single breath or several breaths taken at a predetermined time after administration of isoniazid and/or urea may be used to determine the existence or absence of an active *M. tuberculosis* infection and optionally, its sensitivity or resistance to isoniazid.

In an alternative aspect of the invention, in order to determine that a *M. tuberculosis* infection is present in the lungs (or other tissues), measurements of isotopically labeled nitrogen-15, carbon-13 and/or oxygen-17 or oxygen-18 in the breath of the tested subject are made and compared with concentrations of the naturally occurring nitrogen-14, carbon-12 and/or oxygen-16 in the breath of the tested subject. A single breath or a number of breaths at a predetermined time based upon the time of administration of isoniazid and/or urea to the subject may be used to diagnose the subject. Alternatively, a number of breaths at different times may be used in diagnosis. The ratio of an isotopically labeled element(s) to non-isotopically labeled element(s) may be determined and compared to a predetermined reference or control value (ratio of the same elements) determined from the subject prior to administration of isoniazid and/or urea. A single measurement obtained from the subject which evidences a ratio above the reference ratio will be evidence of the existence of infection and/or sensitivity to isoniazid. A measurement of approximately the reference ratio will be evidence of no infection or inactive *M. tuberculosis* or, in the case of infection (urea positive), but no activity from isoniazid (isoniazid negative), the existence of an *M. tuberculosis* infection with a strain which is isoniazid resistant.

Figure 2:
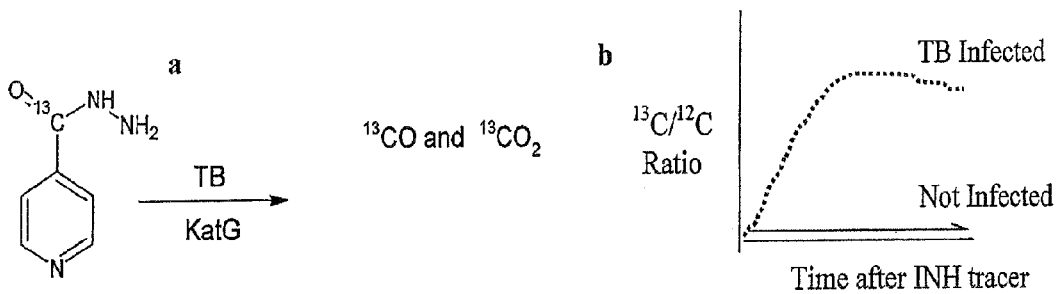
FIG. 2 shows a) TB specific metabolism of $^{13}C$—INH to products (carbon monoxide and carbon dioxide) and b) the mechanism for readout of infection. Note that the predominant gas which is exhaled from an infected subject in this aspect of the invention is carbon monoxide, with a minor amount of carbon dioxide. Converting carbon monoxide to carbon dioxide and measuring all carbon dioxide exhaled may provide greater accuracy in diagnosis.
Figure 3:
FIG. 3 shows a diagram how labeled urea may be delivered to the lung of a subject to be diagnosed.
Figure 4:
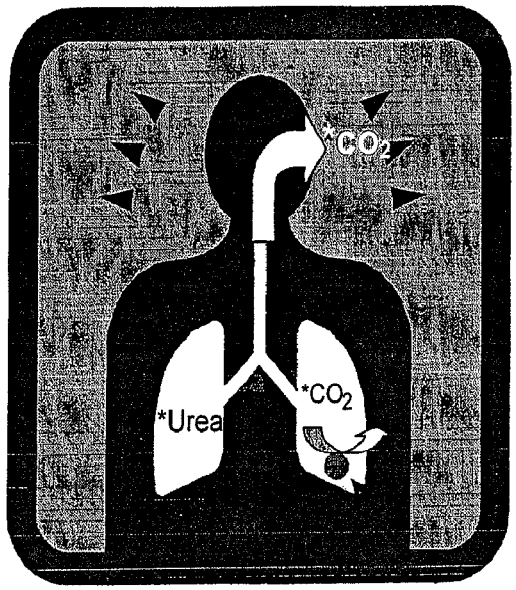
FIG. 4 shows a diagram representing how urease converts labeled urea to labeled carbon dioxide in the lungs of a TB positive subject. Detection of labeled $CO_2$ indicated TB infection.

In alternative embodiments, a number of breaths at different times may be taken from the subject and a graph or curve may be generated showing the ratio of the isotopically labeled element to the naturally occurring elements in the breath of the tested subject as a function of time. A curve showing an increase in the ratio of the isotopically labeled element to non-isotopically labeled element over time (compared to a control with no infection) is evidence of the existence of a *M. tuberculosis* infection. FIGS. 1*b* and 2*b* show an exemplary graph generated by comparing the ratio of nitrogen-15/nitrogen-14 or carbon-13/carbon-12 in the exhaled breath of the subject to be diagnosed is/are made. The concentrations of isotopically labeled elements in the samples are compared to a standard ratio which may be obtained from a control group, or more preferably, from the subject prior to administration of isoniazid and/or urea.

A curve may be fitted to the measured concentrations and then analyzed, preferably by determining the rate of rise of the curve, or by the magnitude of the plateau. Such an analysis indicates the level of activity of *M. tuberculosis* species in the subject, which can be used to diagnose the presence of *M. tuberculosis* in the lungs (or other tissues) of the subject.

Preferably at least a majority of the exhaled breaths, and most preferably every exhaled breath at a predetermined time for a predetermined period, is sampled for that period or until the determination of the level of *M. tuberculosis* activity has reached a preset accuracy.

A predetermined time period after administration of isoniazid and/or urea to a subject may be used to provide a highly accurate measure of diagnostic value. This period may be determined by using a sample of control subjects (with and without *M. tuberculosis* infection) who have been administered isotopically labeled urea and/or isoniazid and then measuring isotopically labeled elements in the exhaled breath of the subjects after identified periods of time. The predetermined period of time that period during which samples of a subject are taken after administration Following the step of orally administering the isoniazid/urea to the subject, the exhaled breath of the subject is analyzed to detect a cleavage product or products, which indicate the presence of *M. tuberculosis* in the lungs or other tissue of the subject. The product or products are detected by analyzing a gas sample of the exhaled breath of the subject with a measuring instrument (or a urine, serum or plasma sample for analyzing nitrite or nitrate levels from isoniazid cleavage). Such a gas sample can be obtained in a number of ways including, but not limited to, having the subject exhale or blow into a tube connected to the measuring instrument. A breath collection bag, a glass vial containing a septum or a nasal cannula is used. The subject breaths directly into the breath collection bag or through the septum into the glass vial. In the case of the nasal cannula, such a cannula includes a section of tubing, usually plastic, with two prongs. Each prong is inserted into a nostril and the cannula is then connected to the measuring instrument. As the subject exhales through the nose, the exhaled air flows through the cannula to the measuring instrument.

The type of measuring instrument used to detect the product or products depends upon the type of label. Preferably, the instrument is a mass spectrometer gas analyzer, or an infrared laser spectrometer. For example, if a nitrogen-15 or carbon-13 (oxygen-17 or oxygen-18) isotopically-labelled substrate is used, the nitrogen-15 or carbon-13 (oxygen-17 or oxygen-18) isotopically-labelled cleavage product or products can be detected by using a measuring instrument including, but not limited to a mass spectrometer or a gas analyzer, which is sensitive to the nitrogen-15 or carbon-13 (oxygen-17 or oxygen-18) isotope. The ratio of the concentration of carbon-13 or nitrogen-15 (oxygen-17 or oxygen-18) isotopically-labelled cleavage product or products to the concentration of carbon-12 or nitrogen-14 (oxygen-16) cleavage product or products is then determined. Since nitrogen-14 and carbon-12 and oxygen-16 are the more abundant isotopes in nature, nitrogen-14, carbon-12 and oxygen-16 atoms are more abundant in unlabelled molecules which are found in the exhaled breath of a patient or subject. Thus, a higher carbon-13/carbon-12, nitrogen-15/nitrogen14, or oxygen 17-18/oxygen-16 ratio determined indicates a higher concentration of the carbon-13, nitrogen-15, oxygen-17 or oxygen 18 isotopically-labelled cleavage product or products, which positively indicates the presence of *M. tuberculosis* in the lungs (or other tissues) of the subject. It is noted that the ratio (isotopically-labeled atom/non-isotopically labeled atom) obtained after administration of isoniazid may be used to determine the sensitivity of *M. tuberculosis* to isoniazid.

Preferably, at least one of the cleavage products of isoniazid is nitrogen-15 isotopically labeled nitric oxide (NO) and urea is carbon-13 isotopically-labelled carbon dioxide. Examples of measuring instruments which can be used with carbon-13 isotopically-labelled carbon dioxide include, but are not limited to, an infrared spectrometer and an isotope ratio mass spectrometer. The infrared spectrometers are well known in the art, and have the advantage of being both rapid and accurate, as well as sensitive. Examples of such infrared spectrometers are disclosed in U.S. Pat. No. 5,063,275, which is incorporated by reference herein.

Alternatively, an analytical assay is described which is based on the use of nitrogen-15 labeled expired nitric oxide (NO) or C-13 labeled expired $CO_2$ in the present assay. In this method, isotope ratio mass spectroscopy (IRMS) is used as a detection method for N-15, C-13 (also O-17 or O-18) which occurs naturally in expired breath of a subject. A particularly preferred mass spectromer is a Finnegan Delta Plus XL, which is an isotope ratio mass spectrometer. Non-dispersive infrared spectroscopy (NDIRS) analysis and analysis methods which are well known in the art also may be employed.

A representative test protocol for the present invention is as follows: isotopically labeled isoniazid and/or urea is administered to a subject or patient to be tested. The administration may be by oral or preferably by pulmonary administration, as described in greater detail herein, using an inhaler or other device adapted to deliver an effective amount (generally, an effective amount within the range of about 0.05 to about 25 mg, about 0.25 to about 10 mg, about 0.5 to about 8 mg, about 0.5 to about 5 mg, about 0.75 to about 3 mg) of isotopically labeled isoniazid and/or urea, preferably isotopically labeled isoniazid (preferably nitrogen-15 isotopically labeled isoniazid) and urea (preferably carbon-15 isotopically labeled urea) to the lungs of the patient or subject. After an appropriate period of fasting and prior to administration of isoniazid and/or urea, in certain instances, a number of breaths are taken for the subject at a predetermined time to produce a "control ratio" or baseline ratio of isotopically labeled atom to non-isotopically labeled atom. Alternatively, a control ratio for a predetermined time period may be determined using a control population, rather than the subject of the diagnosis. Just prior to the taking of breath samples, a dose of nitrogen 15 labeled isoniazid and/or carbon-13 labeled urea is administered to the subject to be tested either orally or by a pulmonary, preferably intratracheal route. Breath samples from the subject are collected after a predetermined time, with the predetermined time being significantly different for oral administration versus pulmonary administration of isoniazid and/or urea. Ratios of isotopically labeled atoms to non-isotopically labeled atoms are measured/determined from the breath of the subject to be diagnosed and this ratio is then compared to the "control ratio". A measured ratio which is significantly higher than the control ratio is evidence of infection by *M. tuberculosis*. In instances where the measured ratio of isotopically labeled atom to non-isotopically labeled atom after administration of isoniazid and/or urea is higher than the control ratio, then *M. tuberculosis* infectivity is made out. In instances where cleavage of urea occurs, but where no activity against isoniazid occurs, then the presence of a isoniazid resistant strain of *M. tuberculosis* is diagnosed.

Advantages of this test are the following: it is practical, sensitive and specific; the validity of the test is not influenced by stress, exercise, hormone imbalances, or some drugs and medications it is a non-invasive method; it is simple to perform and can be readily used in physicians' offices or medical laboratories; it is safe since carbon-13, nitrogen-15, and oxygen-17 and -18 are naturally occurring isotopes found in all carbon-containing and nitrogen-containing substances; it involves no radioactivity, and may be used in children and women.

The carbon-13/nitrogen-15 (urea/isoniazid or isoniazid/urea) test is safe, reliable, and specific in diagnosis of tuberculosis and measurement of the severity of TB in patients. The invention is also preferred to diagnose TB diabetes and to monitor TB in TB positive patients, especially those who are being treated with antibiotics. A preferred embodiment of the invention is a kit containing the necessary material for performing the described method. This kit may contain but is not limited to a source of nitrogen-15, carbon-13, oxygen-17 and/or oxygen 18 isotopically labeled isoniazid and/or urea as an oral or pulmonary dosage form; and a breath collection device. The kit may also contain a set of patient instructions for its use. In another embodiment, the kit may additionally contain a blood collection device such as a lancet or hypodermic needle and vacutainer or a urine collection vial or other container for the additional determination of blood (serum or plasma) or urine levels of nitrite and/or nitrate.

Alternatively and preferably, at least one of the cleavage products is nitrogen-15 isotopically-labelled nitric oxide (NO, from isoniazid) or ammonia ($NH_3$, from urea). Of course, both carbon-13 isotopically-labelled carbon dioxide and nitrogen-15 isotopically-labelled ammonia could be present, providing that the substrate has both labels. Both ammonia and carbon dioxide have the advantage of being molecules which are present in the exhaled breath of the subject.

Figure 5:
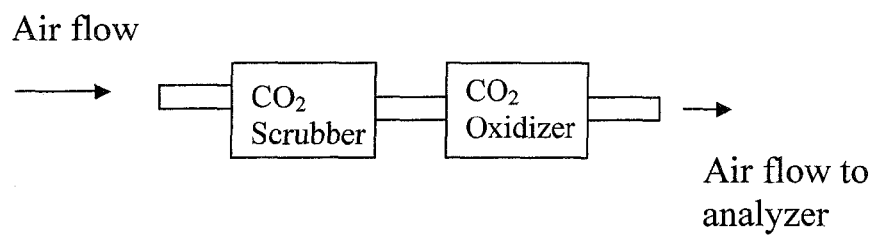
FIG. 5 shows a diagram of pretreatment steps on a sample to remove $CO_2$ before conversion of CO to $CO_2$ in a diagnostic test pursuant to the present invention.

In certain instances, the isoniazid may be labeled with carbon 13, such that the cleavage product is isotopically labeled carbon monoxide (CO). The isotopically labeled carbon monoxide may be measured directly or alternatively, converted to isotopically labeled carbon dioxide and measured. Ratios of isotopically labeled carbon-13 to non-isotopically labeled carbon-12 in the sample breaths may be determined and compared to control ratios. In other instances, the isoniazid may be labeled with oxygen 17 or 18, such that the cleavage product is isotopically labeled carbon monoxide (CO). The isotopically labeled carbon monoxide may be measured directly or alternatively, converted to isotopically labeled carbon dioxide and measured. Ratios of isotopically labeled oxygen 17 or 18 to non-isotopically labeled oxygen 16 in the sample breaths may be determined and compared to control ratio The ratio of $^{13}CO$ to $^{12}CO$ in the CO produced from KatG activation of INH within the bacterium and then exhaled can be examined directly by mass spectrometry or laser spectroscopy. If desired, it can also be oxidized quantitatively by many known oxidants to $CO_2$, and the ratio of $^{13}CO_2$ to $^{12}CO_2$ determined by mass spectrometry or laser spectroscopy: such a suitable oxidant would be to pass the gas stream though a filter pad impregnated with Palladium Chloride solution. If desired, the $CO_2$ in the gas stream can be removed by many known $CO_2$ scrubbing reagents before conversion of CO to $CO_2$, thus providing an improved background for detection of the CO. See, Allen and Root. "Colorimetric determination of carbon monoxide in air by an improved palladium chloride method." Journal of Biological Chemistry 216 309-317 (1955). Additionally, if another labeled compound that produced labeled $CO_2$ has been administered (such as urea for urease assay of *M. tuberculosis*), part of the gas sample would be analyzed for the ratio of $^{13}CO_2$ to $^{12}CO_2$ as normally, and another portion having the $CO_2$ removed before conversion of CO to $CO_2$. Such a schematic device is shown in FIG. 5. Similar schemes can be conducted to analyse CO that is labeled with 17 or 18 O.

Although a number of instruments may be used to measure cleavage products in the present invention, certain characteristics of the measuring device are important. For example, the measuring instrument used to detect the cleavage product or products should have a number of characteristics. The measuring instrument should be able to measure the concentration of the product or products extremely rapidly. Furthermore, either the measuring instrument itself, or an associated device, should be able to perform the associated analysis, including providing a readout or in the case where a curve is to be generated, generating the curve and fitting the curve and providing the analysis of the curve. Such analyses must be performed rapidly. Preferably, the measuring instrument, alone or in conjunction with the associated device, should be able to measure the concentration and perform the associated analysis within about 10 seconds, and most preferably within about 3 seconds, particularly if substantially every exhaled breath of the subject is to be analyzed.

The term "predetermined time", "predetermined period" or "predetermined time period" (all of which may be used interchangeably within the context of their use in describing the present invention) is used to describe a previously determined (using a control group) period of time or periods of time at which exhaled breaths (or urine, serum or plasma samples) are collected from a subject after administration of isoniazid and/or urea in order to analyze for cleavage products to determine whether or not the subject has active *M. tuberculosis*. In the case of isoniazid and/or urea which has been administered using pulmonary administration, the predetermined time (period of time collecting exhaled breaths from a subject) may be a about 15 second to about 10 minutes, about 30 second to 5 minutes, about 45 seconds to 4 minutes, about one minute to 3 minutes, said time period being initiated any time from about 30 seconds to about an hour, about 1 minute to about 30 minutes, about 2 minutes to about 15 minutes about 3 minutes to about 10 minutes, about 4 minutes to about 7 minutes after pulmonary administration of isoniazid and/or urea administration. In the case of oral administration, the predetermined time period for collecting exhaled breaths from a subject may be initiated from about 5 minutes to about 5 hours after administration, about 10 minutes to about 2 hour, about 15 minutes to about 1 hour, about 15 minutes to about 1 hour, about 20 minutes to about 45 minutes, about 25 minutes to about 35 minutes after administration.

After oral or pulmonary administration, isotopically labeled cleavage products such as nitrites and nitrates from isoniazide cleavage may be analyzed from urine, serum or plasma samples.

Thus, the predetermined time period refers to the length of a time period at a particular time (generally after an event, especially the administration of isoniazid and/or urea) required for a cleavage product or products to form and to be exhaled in the breath (or found in the urine, serum or plasma) of the subject. Thus, a number of events must occur. First, the administered isoniazid and/or urea must be accessible to *M. tuberculosis* in the lungs (or other tissues). Then, the administered isoniazid/urea must be cleaved by the enzymes of *M. tuberculosis* to form a cleavage product or products. The cleavage product or products must be absorbed into the blood and then pass into the lungs. Next, the cleavage product or products must be exhaled in the breath of the subject. Finally, the presence of the cleavage product or products must be detected in the exhaled breath.

Furthermore, the predetermined time period should be such that enough breaths are taken to determine a ratio of isotopically labeled elements to non-isotopically labeled elements in the exhaled the breaths from the subject. These may be compared to a control ratio (from the subject or a control group, as otherwise described herein) from which a diagnosis of *M. tuberculosis* infection or isoniazid-resistant *M. tuberculosis* infection is made. In other embodiments there may be more than one time period such that a series of measurements are made and form the basis for the curve of measured concentrations. In this aspects which relies on multiple measurements (time periods) the concentration will rise rapidly initially so that the fitted curve is substantially linear, and will then plateau after about 10-30 minutes, as the process of formation and exhalation of cleavage product or products reaches a steady state. Eventually, as the administered isoniazid/urea is cleaved, the concentration of cleavage product and isotopically labeled element will decrease. The analysis is preferably performed before the curve of measured values reaches a plateau.

The term "control ratio" signifies the ratio of isotopically labeled element to non-isotopically labeled element in a sample obtained from the subject prior to administration of isoniazid and/or urea or a similar ratio obtained from a control population, rather than the subject.

This fitting and analysis of a curve of measured concentrations may be preferred over other approaches. However, the method of the present invention allows repeated breath samples to be rapidly obtained either within a single time period or multiple time periods and then maximizes both the speed and the accuracy of analysis by providing a one point reference number (for the single time period analysis) above which diagnosis of active infection may be made or in the case of multiple time periods, fitting the measured values to a curve and then calculating the rate of increase of the curve, which evidences the infection and its intensity.

Any method for identifying the concentration of isotopically labeled nitric oxide, carbon monoxide (from isoniazid), carbon dioxide (from cleavage of urea or from conversion of carbon monoxide to carbon dioxide from isoniazid) and/or ammonia (from cleaveage of urea) gas can be used to determine the existence (or absence) of *M. tuberculosis* in the lungs (or other tissues) of a patient or subject. The measurement of isotopically labeled gas as a cleavage product by action of *M. tuberculosis* on isoniazid and/or urea is evidence of the existence (or absence) of *M. tuberculosis* in the lungs (or other tissues) of the subject or the existence (or absence) of an isoniazid resistant strain of *M. tuberculosis* in the lungs (or other tissues) of the subject. Thus, where both isotopically labeled isoniazid and urea are administered to a subject to be diagnosed, evidence of cleavage of neither urea nor isoniazid is strong evidence of the subject being *M. tuberculosis* free, evidence of cleavage of urea but not isoniazid indicates the existence of an isoniazid resistant strain of *M. tuberculosis* and evidence of cleavage of both urea and isoniazid is evidence of the existence of a strain of *M. tuberculosis* which may be treated with isoniazid.

In the present invention it is preferred to determine a ratio of an isotopically labeled element (carbon, nitrogen, oxygen) to a non-isotopically labeled element in a cleavage product (gas) being analyzed. For example, if nitric oxide (NO) is being measured as a cleavage product pursuant to isoniazid administration, a ratio of nitrogen-15 to nitrogen-14 in nitric oxide obtained from the breath of a subject is determined. This may be determined readily using mass spectroscopy or infrared laser spectroscopy. In preferred aspects of the invention, a ratio of nitrogen-15 to nitrogen-14 in nitric oxide exhaled by a subject to be diagnosed before administration of isoniazid is determined as a baseline ratio. This ratio appears in the graph of FIG. 1*b* as the X-axis. This ratio is generally below 1%

Specifically, an exemplary method of analysis involves the following steps. A plurality of samples of exhaled breath of the subject is collected rapidly, on the order of one sample about every few seconds or so, preferably such that at least a majority, and most preferably substantially all of the exhaled breaths of the subject at a predetermined time for a predetermined period(s) are sampled. Next, the concentration of a cleavage product is measured and the concentration of an isotopically labeled element, such as nitrogen-15, carbon-13, oxygen-17 or oxygen-17 is compared with its naturally occurring counterpart (e.g. respectively, nitrogen-14, carbon-12 and oxygen-16) in the breath of the subject. Where the ratio of isotopically-labeled element to naturally occurring element is approximately 0 or approximately a control ratio (the control ratio is based upon measurements taken in the subject prior to administration of isoniazid and/or urea), then *M. tuberculosis* is not present. In cases where the ratio of isotopically-labeled element to naturally occurring element is above a predetermined value (e.g. established from control groups) measurements above the predetermined value and/or increases of the ratio as a function of time, evidences the existence of *M. tuberculosis*.

Although measuring and analyzing exhaled breaths from a subject for a single predetermined period represents a preferred approach to determining the existence or absence of a *M. tuberculosis* infection, alternative approaches also may be used. In instances where a number of measurements of exhaled breath from the subject are taken from different periods, a curve may be fitted or generated from the measured concentrations. A curve may be fitted to the measured concentrations, for example, as depicted in FIGS. 1*b* and 2*b*. If the ratio remains flat at the x-axis (essentially 0 or close to 0-based upon the subject or a control group) as a function of time, the presence of *M. tuberculosis* is ruled out. The rate of rise of the curve may be determined by calculating the integral or by derivation (calculation of the derivative), preferably after the measurement of the concentration of cleavage product(s) in each sample. The analysis of the curve indicates the level of *M. tuberculosis* activity in the lungs of the subject. A rapid rise in the measured concentrations (a steeper curve), would evidence a high level of *M. tuberculosis* activity in the subject, whereas a slower rise in the measured concentrations (a shallower curve) would evidence a lower level of *M. tuberculosis* activity. If the *M. tuberculosis* infection is systemic, a greater period of time will be required for absorption and distribution of the labeled compound to the site of infection and release of labeled gasses. The technique will also prove useful in monitoring the responses of the TB infection to drugs, if the drugs are effective then the bacterial load (measured as either the rate of labeled gas increase, or the value of the plateau, will continue to decrease—if the drugs are ineffective due to resistance, then this will not happen and so alternative drug therapies used.

In an analogous manner, if isotopically labeled isoniazid and urea (preferably having different elements labeled so that cleavage products of isoniazid will be distinguishable from cleavage products of urea) are used, these can provide evidence of the existence (or absence) of *M. tuberculosis* produce concentrations of cleavage products which evidence that urea is being cleaved.

The single point (predetermined time period) approach to diagnostic analysis has a number of advantages, the major ones being the ease of use and rapid nature of the diagnosis. This approach also provides a diagnostic method which can be used in a clinic or even a doctor's office. A single calculation may be made by taking a number of exhaled breaths from the patient or subject for the predetermined period and then analyzing for isotope-labeled elements in the sample, providing a ration of isotopically-labeled elements to non-isotopically-labeled elements and comparing that ratio to a predetermined ratio obtained from the subject or from a control group.

In other approaches, the calculation of a derivative from a graph produced from a number of collection samples (from varying time periods) which provides a number of data points has advantages over other methods of analysis, such as the calculation of an integral. First, the calculation of the derivative does not require a reference breath sample to be obtained before isoniazid/urea is administered to the subject. Since the derivative represents the rate of increase of the measured concentrations of a cleavage product or products, the starting concentration of that cleavage product or products is unimportant. However, the initial concentration of the cleavage product or products in the reference breath sample is important for the proper calculation of the integral, since such an initial concentration represents a background value which must be subtracted from the measured concentrations after administration of the urea.

After the resultant measurement has reached a predetermined level of accuracy, or after a predetermined time period has elapsed, no more samples are collected.

The present method utilizing a breath assay has a number of advantages. First, the exhaled breath of the subject can be analyzed in real time; that is, there is relatively little delay between the time the *M. tuberculosis* activity takes place, and the time such activity is measured. Second, the samples of exhaled breath are obtained rapidly and are analyzed immediately in a manner which substantially increases the accuracy of the results. Depending on method, one or multiple samples may be obtained. In general, a single sample (from a number of exhaled breaths) represents a convenient method which exhibits ease of use and patient compliance. In contrast, obtaining multiple samples from the subject increases the accuracy of the test. There is also less statistical error since many samples are collected. In addition, in this aspect, since samples are preferably collected until a preset level of accuracy is reached, ambiguous results can be substantially eliminated, preventing the need for repeating the test.

The readout of isotopic ratios can be performed by sensitive gas mass spectrometry analysis, but also laser spectroscopy techniques which may allow for more compact and portable devices. In certain aspects of the invention, especially where a ratio of isotopically labeled element to non-isotopically labeled element in a gas is to be used in the analysis, a Finnegan Delta Plus XL™ Mass Spectromer may be used. Collection of exhaled gases (including gaseous cleavage products) from the subject when the cleaved products are gasses may be effected using a standard gas collection bag, using a glass vial with a septum (the subject simply blows into the vial through the septum, or using any other method for collecting breaths from the subject. It is also noted that isotopically labeled nitrogen-15 present in nitrites and nitrates in the urine, serum or plasma of the subject from cleavage of isotopically labeled isoniazid may also be analyzed according to the present invention. A ratio of isotopically labeled nitrogen-15 to non-isotoptically labeled nitrogen in the urine, serum or plasma sample after isoniazid administration may be determined and compared to control levels taken from urine, serum or plasma of the subject prior to isoniazid administration. Alternatively, a control group can be used to establish control levels of isotopically labeled nitrites and nitrites in urine, serum or plasma levels and appropriate ratios for comparison purposes.

In the present method, isotopically labeled isoniazid and/or urea may be administered by oral or preferably, by a pulmonary (e.g. intratracheal) route of administration. In the case of oral administration, isoniazid or urea, alone or in combination are administered orally to a subject to be tested for evidence of *M. tuberculosis* infection. Isoniazid may be administered in standard oral dosage form, preferably as an immediate release dosage form or as an enteric dosage form (especially when administered in combination with urea), in combination with a pharmaceutically acceptable carrier, additive or excipient. Oral formulations of urea may be formulated in enteric dosage form to promote release in the small intestine (duodenum, jejunum, ileum) or in combination with a urease inhibitor to inhibit the action of *H. pyrlori* urease on administered urea prior to its such as acetohydroxamic acid (Lithostat), a bismuth salt such as bismuth nitrate, bismuth carbonate, bismuth salicylate or bismuth citrate, a proton pump inhibitor such omeprazole (Prilosec), esomeprazole (Nexium), lansoprazole (Prevacid), pantoprazole (Protonix) and rabeprazole sodium (Aciphex), or a natural product extract from ranunculus repens, to avoid any action by urease from *H. pylori* in the gastrointestinal tract, more specifically, the stomach.

Thus, the present invention also relates to pharmaceutical compositions in oral dosage form comprising effective amounts of isoniazid, urea and a urease inhibitor, optionally in combination with a pharmaceutically acceptable carrier, additive or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

In preferred aspects of the invention, the isoniazid and/or urea is administered to the lungs of the subject via pulmonary administration, including intratracheal administration. The pharmaceutical composition of the invention for pulmonary administration is usually used as an inhalant. The composition can be formed into dry powder inhalants, inhalant suspensions, inhalant solutions, encapsulated inhalants and like known forms of inhalants. Such forms of inhalants can be prepared by filling the pharmaceutical composition of the invention into an appropriate inhaler such as a metered-dose inhaler, dry powder inhaler, atomizer bottle, nebulizer etc. before use. Of the above forms of inhalants, powder inhalants may be preferable.

When the pharmaceutical composition of the invention is used in the form of a powder, the mean particle diameter of the powder is not especially limited but, in view of the residence of the particles in the lungs, is preferably that the particles fall within the range of about 0.1 to 20 μm, and particularly about 1 to 5 μm. Although the particle size distribution of the powder pharmaceutical composition of the invention is not particularly limited, it is preferable that particles having a size of about 25 μm or more account for not more than about 5% of the particles, and preferably, 1% or less to maximize delivery into the lungs of the subject.

The pharmaceutical composition in the form of a powder of the invention can be produced by, for example, using the drying-micronization method, the spray drying method and standard pharmaceutical methodology well known in the art.

By way of example without limitation, according to the drying-pulverization method, the pharmaceutical composition in the form of a powder can be prepared by drying an aqueous solution (or aqueous dispersion) containing the isoniazid, urea or mixtures thereof and excipients which provide for immediate release in pulmonary tissue and microparticulating the dried product. Stated more specifically, after dissolving (or dispersing) a pharmaceutically acceptable carrier, additive or excipient in an aqueous medium, isoniazid, urea or mixtures of isoniazid and urea in effective amounts are added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like water-miscible alcohols. Ethanol is particularly preferable. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical composition in the form of a powder of the invention can be prepared, for example, by spray-drying an aqueous solution (or aqueous dispersion) containing isoniazid, urea or mixtures thereof and excipients, additives or carriers for microparticulation. The aqueous solution (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using a carrier, additive or excipient and isoniazid, urea or mixtures thereof that can be administered via the lungs, according to known preparation methods.

Furthermore, the inhalant comprising the pharmaceutical composition of the invention is preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: Examples of the compounds to be used include isotopically labeled isoniazid, isotopically labeled urea or mixtures thereof. As propellants, fluorinated hydrocarbons such as HFC-134a, HFC-227 and like CFC substitutes are preferable. Examples of usable solvents include water, ethanol, 2-propanol and the like. Water and ethanol are particularly preferable. In particular, a weight ratio of water to ethanol in the range of about 0:1 to 10:1 may be used.

The aerosol of the invention contains excipient in an amount ranging from about 0.01 to about $10^4$ wt. % (preferably about 0.1 to $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of isoniazid and/or urea which is included in the final composition.

The pharmaceutical compositions of the invention are safe and effective for use in the diagnostic methods according to the present invention. Although the dosage of the composition of the invention may vary depending on the type of active substance administered (isoniazid, urea or mixtures thereof) as well as the nature (size, weight, etc.) of the subject to be diagnosed, the composition is administered in an amount effective for allowing the pharmacologically active substance to be cleaved to cleavage products to be measured. For example, the composition is preferably administered such that the active ingredient can be given to a human adult in a dose of about 0.001 to about 100 mg, about 0.01 mg to about 25 mg, about 0.05 mg to about 15 mg, about 0.1 mg to about 10 mg, about 0.5 mg to about 5 mg, about 1 to about 3 mg, and given in a single dose The form of the pharmaceutical composition of the invention such as a powder, solution, suspension etc. may be suitably selected according to the type of substance to be administered and the action of a target enzyme on isoniazid and/or urea.

As an administration route, direct inhalation via the mouth using an inhaler is usually preferable. Since the pharmaceutical composition of the invention allows direct local administration into the airways and in particular, directly to pulmonary tissue, the active substance contained therein produces immediate effects. Furthermore, the composition is formulated as an immediate release product so that cleavage and analysis can begin soon after administration.

Advantages

The present invention allows diagnosis of a *M. tuberculosis* infection, including an isoniazid *M. tuberculosis* infection in a simple diagnostic test, including a breath test. The diagnosis is rapid and effective and displays a number of ancillary advantages as well.

The present invention allows the use of BCG vaccination without compromising the sensitivity or reliability of the tuberculosis test. BCG vaccination is widely used outside the US and shows good protection against TB. Although there is some contention that the BCG vaccine may not be as protective as once thought, that analysis may merely reflect the fact that data on BCG vaccine efficacy come from poorly controlled studies in areas of the world where spontaneous exposure to environmental mycobacteria already boosts resistance to infection among the local populations. In such populations, determination of the efficacy of vaccination may not be reliable. However, a subject coming to an area where tuberculosis infection is common would normally not be protected by the environmental exposures and BCG vaccination would be of benefit in protecting that subject or subjects from infection. In addition, BCG has been shown in some subjects to be a booster of general immunity and has had positive effects on prostate cancer and other conditions. Physicians in third world countries insist on the protective value of BCG and most of the world is vaccinated with BCG. The present invention would replace the reliance on the PPD skin test and thus allow vaccination of populations with BCG without compromising a sensitive, specific, and reliable detection of TB infection.

The present invention represents a rapid, one-stop, easily administered test. The skin tuberculin test has to be carefully administered and read by an expert 3 days after administration. This creates logistical issues. The present diagnostic test would be administered 'all in one go' obviating needs for precise recall. This would allow faster treatment of infected and potentially infectious patients, so preventing the spread of disease more optimally. Finally, administration of a tracer tablet and collecting breath or urine afterwards needs lower level medical skills, making widespread testing by paramedics possible. Samples can easily be mailed to central facilities.

Minimize Unnecessary Chemoprophylaxis. Typically, after a positive skin tuberculin test after overseas deployment, soldiers are given 6 to 12 month courses of isoniazid. Since this test is not specific for TB, and since these long courses have significant effects (hepatotoxicity), therapy compliance can be low (resulting in potentially untreated TB); alternatively in the case of a false-positive test where isoniazid is taken, significant unnecessary toxicities result. Because our test will be much more specific, this will minimize these issues.

Allows Rapid Detection of Resistance Development The predominant mechanism of resistance to INH is mutations affecting mycobacterial peroxidase KatG. Thus, upon resistance, the amount of KatG mediated INH-derived volatiles will change, and so development of INH resistance can also be monitored with this technique.

The following examples provide insight into the use of the present invention. The examples are simply that, exemplary, and are not to be construed to limit the present invention in any way.

EXAMPLES

Administration of Diagnostic Test for Presence of *M. tuberculosis* Infection

There are a number of potential embodiments of the diagnostic assay

Example 1

Inhaled Administration of Labeled Tracer

A. A first embodiment is to administer $^{13}$C-urea by inhalation (such as a dry powder inhaler as desdribed above) in an amount of 0.1 to 10 mg, and the ratio of $^{13}CO_2$ to $^{12}CO_2$ in exhaled breath sample 1 to 60 minutes afterwards (to allow for conversion) is determined by mass spectrometry or laser spectroscopy. The ratio of $^{13}CO_2$ to $^{12}CO_2$ is compared to that of a breath sample obtained before compound inhalation, and an increase in this ratio is indicative of *M. tuberculosis* infection.

B. A second embodiment relates to replace the use of urea with the use of $^{13}$C-Acyl INH as in the example A. above, with analysis of the ratio of $^{13}$Co to $^{12}$CO in exhaled breath sample 1 to 60 minutes after is determined by mass spectrometry or laser spectroscopy. The ratio of $^{13}$Co to $^{12}$CO is compared to that of a breath sample obtained before compound inhalation, and an increase in this ratio is indicative of mycobacterial disease that is likely to be INH-sensitive.

C. Another embodiment is to administer both $^{13}$C-urea and $^{13}$C-acyl INH as in 1(i) and independently analyse of the ratio of $^{13}$CO to $^{12}$Co and of $^{13}CO_2$ to $^{12}CO_2$ in exhaled breath sample 1 to 60 minutes after is determined by mass spectrometry or laser spectroscopy. The ratio of $^{13}$CO to $^{12}$CO (from INH) and $^{13}CO_2$ to $^{12}CO_2$ (from urea) is compared to that of a breath sample obtained before compound inhalation, and so determination of mycobacterial disease and likely sensitivity to INH can be simultaneously determined. If desired, the CO can be analyzed after its oxidation to $CO_2$ as described by D. If desired, other analytes may be measured, such as nitrates or nitrites in a blood sample (serum, plasma), or a urine sample, and analysis performed.

Example 2

Oral Administration of Labeled Tracer

1) Oral Administration of Labeled Tracer

A.) One approach is to administer $^{13}$C-urea by in an oral dosage in an amount of about 0.1 to 100 mg, and the ratio of $^{13}CO_2$ to $^{12}CO_2$ in exhaled breath sample 1 to 180 minutes (also within the range of about 15-30 minutes to 60 minutes) after administration is determined by mass spectrometry or laser spectroscopy. The ratio of $^{13}CO_2$ to $^{12}CO_2$ is compared to that of a breath sample obtained before compound administration, and an increase in this ratio is indicative of *M. tuberculosis* disease. It may be desirable to preclude the potential for *H. pylori* interference with this assay by either enterically coating the urease capsule/tablet so that labeled urea does not come into contact with *H. pylori* and/or administration of known inhibitors of *H. pylori* urease such as bismuth salts, as otherwise described herein.

B) Another approach is to replace use of urea with the use of $^{13}$C-Acyl INH as in 2(i), with analysis of the ratio of $^{13}$CO to $^{12}$CO in exhaled breath sample 1 to 200 minutes after is determined by mass spectrometry or laser spectroscopy. The ratio of $^{13}$Co to $^{12}$CO is compared to that of a breath sample obtained before compound administration, and an increase in this ratio is indicative of *M. tuberculosis* disease that is likely to be INH-sensitive.

C) Another is to administer both $^{13}$C-urea and $^{13}$C-acyl INH as in 2(i) and independently analyse of the ratio of $^{13}$Co to $^{12}$CO and of $^{13}CO_2$ to $^{12}CO_2$ in exhaled breath sample 1 to 120 minutes after is determined by mass spectrometry or laser spectroscopy. The ratio of $^{13}$CO to $^{12}$CO (from INH) and $^{13}CO_2$ to $^{12}CO_2$ (from urea) is compared to that of a breath sample obtained before compound administration, and so determination of *M. tuberculosis* disease and likely sensitivity to INH can be simultaneously determined. If desired, the CO can be analyzed after its oxidation to $CO_2$ as described by Allen and Root, *Journal of Biological Chemistry*, 216 309-317 (1955), relevant portions of which are incorporated by reference herein.

The terms and expressions that have been employed in this application are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

The invention claimed is:

1. A method for diagnosing the presence of *Mycobacterium tuberculosis* in the lungs or other tissues of a patient or subject, including the steps of:
   (a) administering effective amounts of isotopically labeled isoniazid and/or urea to the patient or subject, said isoniazid and said urea being cleavable by *M. tuberculosis* to provide at least one isotopically labeled cleavage product in the breath of said patient or subject, said cleavage product being selected from the group consisting of nitric oxide, ammonia carbon monoxide, carbon dioxide and mixtures thereof;
   (b) collecting breath samples from the patient or subject; and
   (c) analyzing said samples to determine a concentration or concentrations of said cleavage product(s), said concentration(s) indicating the presence or absence of *M tuberculosis* including optionally, the presence of isoniazid resistant *M.tuberculsosis* in the lungs or other tissues by virtue of isoniazid-resistant *M. tuberculosis* not cleaving isoniazid.

2. The method according to claim 1 wherein said breath sample is taken for a predetermined time.

3. The method according to claim 1 wherein said isoniazid is isotopically labeled with nitrogen-15, carbon-13, oxygen-17 or oxygen-18.

4. The method according to claim 1 wherein said urea is isotopically labeled with carbon-13, nitrogen-15, oxygen-17 or oxygen-18.

5. The method according to claim 1 wherein isoniazid and urea are coadministered to said subject.

6. The method according to claim 1 wherein said isoniazid and/or urea arc administered by oral or pulmonary administration.

7. The method according to claim 1 wherein isoniazid is isotopically labeled with nitrogen-15.

8. The method according to claim 1 wherein said urea is isotopically labeled with carbon-13.

9. The method according to claim 1 wherein said isoniazid is isotopically labeled with nitrogen-15 and said urea is isotopically labeled with carbon-13.

10. The method according to claim 1 wherein said isoniazid is isotopically labeled with carbon-13 and said urea is isotopically labeled with nitrogen-15.

11. The method according to claim 1 wherein said isoniazid and said urea arc both isotopically labeled with either carbon-13 or nitrogen-15.

12. The method according to claim 1 wherein said analyzing step comprises comparing at least one ratio of isotopically labeled element(s) to non-isotopically labeled element(s) in said exhaled breath of said patient or subject to a control ratio of isotopically labeled elements) to non-isotopically labeled element(s) in the exhaled breath of said patient or subject or a control group prior to administration of isoniazid and/or urea.

13. The method according to claim 1 wherein said isoniazid and/or urea are administered by pulmonary route of administration.

14. The method according to claim 1 wherein said isoniazid and/or urea are administered by oral route of administration.

15. The method according to claim 1 wherein said urea is administered by oral route in combination with a urease inhibitor.

16. The method according to claim 1, wherein said urea is administered by oral route in an enteric capsule.

17. The method according to claim 1 wherein isotopically labeled isoniazid and isotopically labeled urea are both administered to said subject, and wherein the absence of isoniazid and urea cleavage products is evidence of the absence of *M. tuberculosis* in said subject.

18. The method according to claim 1 wherein isotopically labeled isoniazid and isotopically labeled urea are both administered to said patient, and wherein the presence of isoniazid cleavage product(s) and urea cleavage product(s) is evidence of the presence of isoniazid-sensitive *M. tuberculosis* in said subject.

19. The method according to claim 1 wherein isotopically labeled isoniazid and isotopically labeled urea arc both administered to said patient, wherein the absence of isoniazid cleavage product(s) and the presence of urea cleavage product(s) is evidence of the presence of isoniazid-resistant *M. tuberculosis* in said subject.

20. The method according to claim 1 wherein said carbon monoxide is further converted to carbon dioxide for analysis.

21. The method according to claim 1 wherein said urea is cleaved to produce carbon dioxide or ammonia.

22. The method according to claim 1 wherein said analyzing steps further comprises the steps of fitting the concentrations obtained to a curve; and analyzing the curve or a plateau of said curve to determine the extent of infection.

23. A single dose composition adapted for pulmonary administration to a patient or subject to be diagnosed for the existence or absence of isoniazid resistant *M. tuberculosis*, said composition comprising a diagnostic effective amount of isotopically labeled isoniazid and urea, in combination with a pharmaceutically acceptable excipient, a propellant and optionally, a solvent and a dispersant, said composition being further adapted for single use only.

24. A kit comprising a single dose composition of isotopically labeled isoniazid and/or urea adapted for pulmonary administration in amounts effective to diagnose the existence of *M. tuberculosis* in a patient or subject if present; a collection bag or vial to collect the breath of said patient or subject after administration of said isoniazid and/or urea; and an instruction manual.

25. The method according to claim 1 wherein said analyzing step comprises comparing at least one ratio of isotopically labeled element(s) to non-isotopically labeled element(s) in said exhaled breath of said patient or subject to a predetermined value.

26. The method according to claim 25 wherein said predetermined value is a control ratio of isotopically labeled elements) to non-isotopically labeled element(s) in the exhaled breath of said patient or subject.

27. The method according to claim 25 wherein said predetermined value is a control ratio of isotopically labeled element(s) to non-isotopically labeled element(s) in the exhaled breath of a control group.

28. The method according to claim 1 wherein in said cleavage product is nitric oxide, ammonia or mixtures thereof.

29. The method according to claim 1 wherein said cleavage product is carbon monoxide, carbon dioxide or mixtures thereof.

* * * * *

UNITED STATES PATENT AND TRADEMARK OFFICE
CERTIFICATE OF CORRECTION

| | | |
|---|---|---|
| PATENT NO. | : 7,897,400 B2 | |
| APPLICATION NO. | : 11/955773 | |
| DATED | : March 1, 2011 | |
| INVENTOR(S) | : Graham Timmins and Vojo P. Deretic | |

It is certified that error appears in the above-identified patent and that said Letters Patent is hereby corrected as shown below:

Column 21, Line 52: "urea arc both" should be --urea are both--.

Column 21, Line 58: "elements)" should be --element(s)--.

Signed and Sealed this
Tenth Day of May, 2011

David J. Kappos
*Director of the United States Patent and Trademark Office*